United States Patent [19]

Tiep et al.

[11] Patent Number: 4,572,177
[45] Date of Patent: Feb. 25, 1986

[54] OXYGEN THERAPY APPARATUS

[76] Inventors: Brian L. Tiep, 632 Norumbega Dr., Monrovia, Calif. 91016; Robert E. Phillips, 12217 Iredell St., Studio City, Calif. 91601; Ben A. Otsap, 7661 Airport Blvd., Los Angeles, Calif. 90045

[21] Appl. No.: 624,414

[22] Filed: Jun. 25, 1984

[51] Int. Cl.$^4$ .............................. A61M 16/00
[52] U.S. Cl. ................ 128/205.17; 128/207.18
[58] Field of Search ............... 128/205.17, 207.18, 128/205.13, 204.18, 203.28

[56] References Cited

U.S. PATENT DOCUMENTS

| 2,352,523 | 6/1944 | Emerson | 128/205.17 |
|---|---|---|---|
| 3,005,453 | 10/1961 | Wellenstein et al. | 128/204.28 |
| 3,102,537 | 9/1963 | Bartlett, Jr. | 128/205.13 |
| 3,170,463 | 2/1965 | Duggan | 128/205.17 |
| 4,120,300 | 10/1978 | Tiep | 128/204.24 |

Primary Examiner—Henry J. Recla
Attorney, Agent, or Firm—Edward D. O'Brian; K. H. Boswell

[57] ABSTRACT

An apparatus for use in oxygen therapy can be constructed so as to include a gas holder appearing more or less as a pendant which includes a variable volume internal chamber and so as to use a line for continuously delivering oxygen to the holder and a conduit for conveying gas between a person using the apparatus and the holder. During use on exhalation the initially exhaled gas will flow through cannula carried by the conduit and the conduit into the holder so as to expand the variable volume chamber. When it is filled the remaining expired gas will be vented to the ambient. As the holder is filled the expired gas within it will be mixed with a limited amount of oxygen and thereafter during exhalation the oxygen supply will displace the expired gas in the conduit so that it flows outwardly from the cannula to be picked up by the expired air being vented to the ambient. On inhalation the oxygen and any non-displaced gas in the conduit will be inhaled preferentially to the ambient air and will be followed into the respiratory track by the gas from within the variable volume chamber and the oxygen concurrently supplied to the holder. During the remainder of inhalation ambient air will be inhaled.

16 Claims, 3 Drawing Figures

OXYGEN THERAPY APPARATUS

CROSS REFERENCE TO RELATED APPLICATIONS

This application is related to the co-pending applications Ser. No. 534,378, filed Sept. 21, 1983 entitled "Oxygen Therapy Method and Apparatus" and Ser. No. 432,187 entitled Oct. 1, 1982 entitled "Oxygen Delivery Apparatus" in the names of the applicants set forth in this application. The entire disclosures of these two co-pending applications are incorporated herein by reference. The applicants in this application claim priority on the basis of both of these two applications for subject matter disclosed herein which is found in either of these prior two applications.

BACKGROUND OF THE INVENTION

The invention set forth in this application pertains to new and improved oxygen therapy apparatus.

For many years it was, and in many hospitals, it still is customary to maintain a given oxygen level in the blood of an individual by constantly and directly supplying oxygen to the individual so that some of such oxygen can be inhaled. With this "direct" procedure various different means such as nasal cannula, masks or tent-like enclosures are from an appropriate source such as a supply tank used to convey and/or confine the oxygen supplied so that it will be inhaled during inhalation. While the procedure of directly supplying oxygen as noted is effective for its intended purpose it is also somewhat wasteful and hazardous. This is because some of the oxygen supplied is vented to the ambient air and because the concentration of oxygen generally within proximity of the patient may be sufficiently high to create a hazard.

It is previously been recognized that the quantity of oxygen required to maintain such a specific oxygen level in the blood can be reduced from that required by the prior "direct" type of procedure by utilizing what may be referred to as an "indirect" type of method. The latter involves utilizing an apparatus generally between the patient and the oxygen source which receives the oxygen supplied for ultimate use by the patient and then transmits it to the patient. This latter method involves capturing the initial portion of the breath exhaled by a patient and then venting the remainder of the exhaled breath to the ambient while concurrently displacing some of the captured, exhaled breath with oxygen. This latter method also involves having the patient next breathing in the oxygen which displaced some of the exhaled breath at the start of inhalation and then breathing in the oxygen supplied to the equipment used and ambient air until the close of the exhalation cycle when inhalation again commences.

Although it is been recognized that a number of differently designed pieces of equipment or apparatuses are at least in theory capable of being utilized in carrying out an indirect procedure as briefly indicated in the preceding for supplying oxygen to an individual up to present time it has been considered that it was preferable to utilize a single specific type of equipment in practicing this indirect method. It is not considered that an understanding of this invention requires a detailed discussion as to why this is the case. It is, however, considered important to note that the particular type of apparatus considered preferable is constructed so as to appear more or less like an inflated, almost balloon-like enlarged handle bar mustache. This "mustache" type of apparatus is worn generally between the upper lip and the nose of a patient and extends along the sides of the cheek of an individual wearing it. It includes nasal cannula used to convey gas to and from the nostrils as the apparatus is used.

Such a "mustache" apparatus is somewhat undesirable from an appearance standpoint and on occasion is not as comfortable to wear as a patient may desire. Further, because of the location where such a mustache device is worn there is always a remote chance that the device may be accidentally or inadvertently disloged from an operative position or otherwise rendered inoperative. Although the chances of this occurring are relatively limited they cannot be completely neglected.

BRIEF SUMMARY OF THE INVENTION

As a result of these latter considerations it is considered that there is a need for a new and improved apparatus for carrying out what was referred to in the preceding as an "indirect" method of delivering oxygen to an individual such as a patient undergoing treatment. This invention is intended to fulfill this need. More specifically it is intended to provide new and improved apparatus for efficiently and effectively carrying out what has been referred to as an indirect method of delivering oxygen, which apparatus is relatively inexpensive to manufacture, is quite reliable when used, may be easily and conveniently employed by or on an individual, is of such a character as to minimize any interference with a person's appearance and is of such a character that when used the chances of the operation of the device being inadvertently or accidentally interfered with are quite minimal.

In accordance with this invention these various objectives are achieved by providing an apparatus which is primarily intended for use in oxygen therapy, said apparatus having a gas holder, said holder having an interior variable volume chamber capable of changing in volume in response to pressure resulting from the inhalation and exhalation of a person who is using said apparatus, a conduit means for conveying gas, an extremity of said conduit means being in communication with the interior of said variable volume chamber, the other extremity of said conduit means being located so as to receive expired air from said person and so as to be capable of supplying gas to said person without completely blocking the flow of ambient air to and from said person, and supply means for supplying oxygen to said conduit means so that it will be supplied to said person during inhalation, said other extremity of said conduit means being spaced so that expired air can be vented to the ambient during part of the exhalation cycle and so that ambient air can be inhaled during part of the inhalation cycle in which the improvement comprises: said holder including a fixed volume chamber located adjacent to said variable volume chamber and opening means leading between said two chambers, said first mentioned extremity of said conduit means and said supply means both leading into said fixed volume chamber, baffle means in association with said fixed volume chamber for directing oxygen from said supply means into said first mentioned extremity of said conduit means, said baffle means being shaped so that when said variable volume chamber is inflated there is substantially no flow of oxygen into said chamber as oxygen flows from said supply means.

Unfortunately a summary of the type set forth in the preceding inherently is incapable of indicating many features and facets of an apparatus which are important or desirable for one or more reasons or of effectively indicating the manner in which the apparatus is used.

BRIEF DESCRIPTION OF THE DRAWING

For these reasons it is considered that the invention described in this specification is best more fully explained with reference to the accompanying drawing in which.

Figure 1:
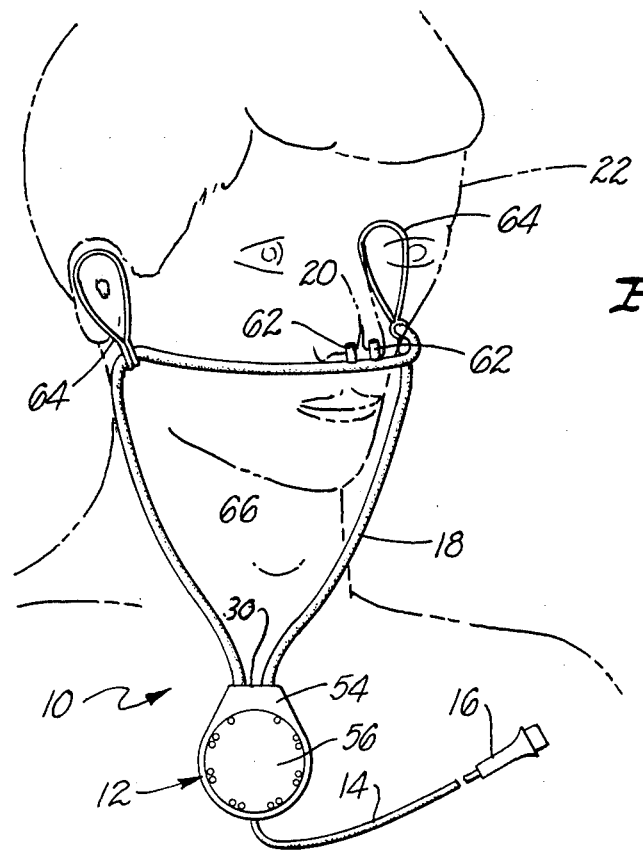
FIG. 1 is a view of a presently preferred embodiment or form of an apparatus of this invention showing this apparatus as it is normally worn by an individual utilizing it, this individual being shown in phantom in this figure.
Figure 2:
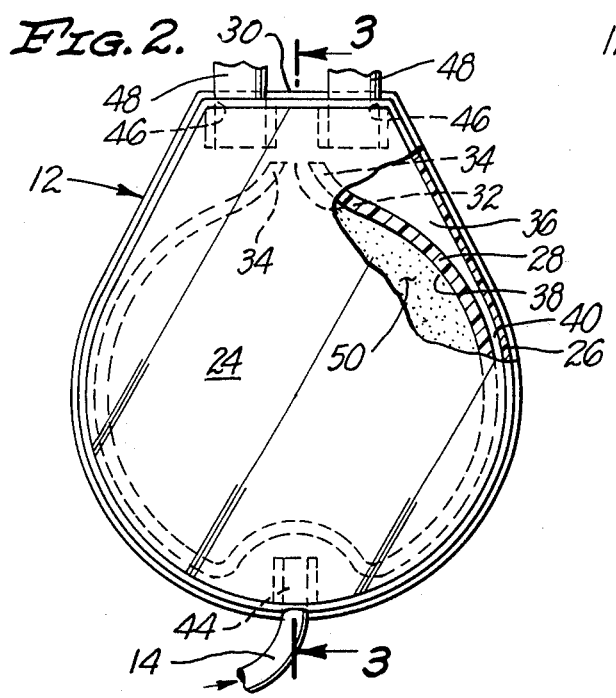
FIG. 2 is a front elevational view of the gas holder forming the principal part of the apparatus shown in the preceding figure, the cover of this gas holder being partially broken away so as to clearly indicated the internal construction within it.
Figure 3:
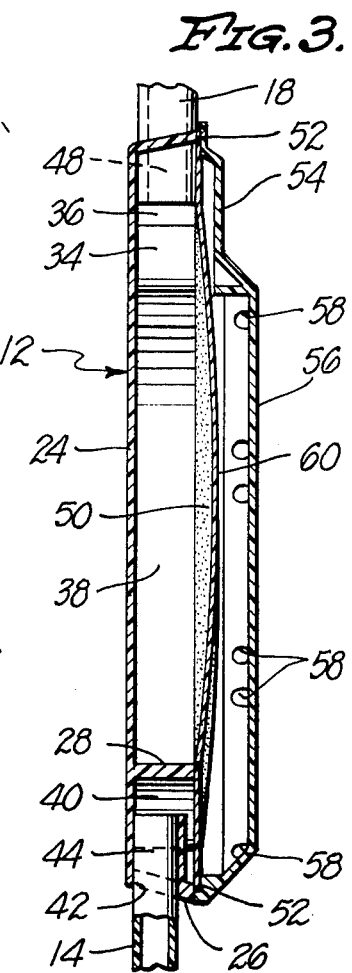
FIG. 3 is a cross-sectional view at an enlarged scale taken at line 3—3 of FIG. 2.

The particular apparatus illustrated utilizes the operative features or concepts of the invention described herein. These features or concepts as are defined or summarized in the appended claims forming a part of the disclosure of this specification. Those skilled in the design and construction of an oxygen therapy apparatus will be able to design other somewhat differently appearing and somewhat differently constructed apparatuses utilizing these concepts or principals on the basis of the disclosure of this specification through the use or exercise of routine skill in the field of their activity. For this reason the invention is not to be considered as being limited precisely to an apparatus as shown in the drawing.

DETAILED DESCRIPTION

In the drawing there is shown an apparatus 10 of the present invention which includes three principal parts. The first of these is a gas holder 12. The second is a flexible tube 14 which is utilized to convey oxygen to the holder 12 from an appropriate source of supply such as, for example, a conmventional tank (not shown). If desired a conventional fitting 16 may be located on the tube 14 so as to facilitate it being connected to either such a tank or to another line (not shown) conveying oxygen. This holder 12 is used for the purpose of conveying oxygen from the tube 14 to a flexible conduit or tube 18 which in turn is used with gases being conveyed to and expired from the nostrils 20 of an individual 22 using this apparatus 10.

The holder 12 is quite important with the present invention. It is formed so as to include a generally flat back 24 carrying an upstanding nearly circular peripheral rim 26. This back 24 also carries an internal nearly circular rim 28 which is spaced from and generally parallel to the rim 26. At the top 30 of the holder 12 an internal opening 32 is defined within the rim 28 by means of curved baffles or baffle like ends 34 on the rim 28. At the top 30 the peripheral rim 26 is distended outwardly from a circular path a comparatively small amount as shown so as to define what is referred to herein as a fixed volume chamber 36. This fixed volume chamber 36 is in communication with a variable volume chamber 38 located generally within the interior of the internal rim 28. The space generally between the two rims 26 and 28 may be referred to as a flow channel 40 which leads generally into the fixed volume chamber 36.

An opening 42 is provided in the rim 26 so as to lead into the flow channel 40 substantially opposite from the fixed volume chamber 36. This opening 42 is adapted to receive an end 44 of the tube 14. Other openings 46 are provided in the rim 26 adjacent to the baffles 34. These openings 44 are adapted to receive ends 48 of the conduit 18 in such a manner that these ends 48 extend into the fixed volume chamber 36 a comparatively short distance as shown. The ends 44 and 48 are sealed to the rim 26 in a conventional manner.

A flexible, easily deformed diaphragm 50 as subsequently more fully discussed is positioned so as to extend generally across the internal rim 28 so as to cover and in effect, serves as a part of the variable volume chamber 38. This diaphragm 50 will normally be sealed in a conventional manner to the rim 28 and to a flat periphery 52 of a cover 54. This cover 54 fits against and extends across the entire peripheral rim 26. This cover 54 has a slightly dome shaped or expanded shaped central portion 56 which extends directly across the diaphragm 50.

Various openings 58 are provided in this portion 56 so as to avoid creating any sort of a sealed relationship within the holder 12 isolating the side 60 of the diaphragm 50 from the ambient air. Because of the fact that the diaphragm 50 is sealed against the internal rim 28 and the periphery 52 the variable volume chamber 38 is, of cource, isolated from the ambient air and from the flow channel 40. It is only in communication with the fixed volume chamber 36 through the opening 32.

Preferably with the invention the conduit 18 is in the nature of a symmetrical loop extending between the ends 48. This construction is preferred since it minimizes the possibility of oxygen being completely cut off from a patient as a result of a portion of the conduit 18 being bent so as to no longer convey a gas. When the conduit 18 is a loop type structure as indicated it may conveniently be held in place by small bands or loops 64 engaging the conduit 18 and holding it around the ears 66 of the individual. Various other holding means than these bands can of course, be employed.

Preferably all of the holder 12 except for the diaphragm 50 ia formed of a comparatively "soft" yet self-supporting material which is of such a character that it will not hurt an individual even if it is pushed up against an individual with significant force. All portions of the holder 12 except the diaphragm 50 must, of course, be sufficiently resistant to crushing so that there is substantially no danger of the holder 12 being completely flattened or otherwise deformed so as to render the diaphragm 50 substantially immobile or so as to interfere with the gas flow in this apparatus 10. It is considered that suitable results can be achieved by manufacturing the holder 12 except for the diaphragm 50 out of a highly plasticized vinyl composition or the like.

The diaphragm 50 should preferably be manufactured out of a comparatively "loose," easily deformed, more or less "floppy" material. This diaphragm 50 should be of such a character that it is capable of being very easily moved in response to the pressures developed in connection with breathing during the use of the apparatus 10 so as to either fit substantially against the back 24 or against the central portion 56 of the cover 54. The amount or force of pressure necessary to move the diaphragm 50 between these two positions should be sufficiently low that the diaphragm 50 can be moved easily between these two position by even a person having respiratory problems. It is possible to form the diaphragm 50 of a somewhat elastomeric or resilient composition so that it will be stretched slightly when it is expanded against the cover 54 for a purpose as hereinafter discussed.

When the apparatus 10 is to be used small cannula or hollow prongs 62 of known design carried by the conduit 18 so as to be in communication with its interior (not numbered) are located so as to extend into the nostrils 20 of the individual 22. These cannula are preferably located so as to cover only the center regions of the nostrils 20 so that inhaled and exhaled gas will preferentially flow from and into them, respectively, before flowing from and to the ambient air.

During the use of the apparatus 10 oxygen at a comparatively low flow rate and at a comparatively low pressure will be continuously supplied through the tube 14 to the holder 12. While the pressure of the oxygen delivered should be comparatively low it must be above the pressure which can be developed by a person breathing. Preferably it is considerably higher than the latter pressure.

At the start of such an exhalation period exhaled gas will be preferentially exhaled into the cannula 62. This exhaled gas will tend to flow in equal amounts to both of the ends 48 of the conduit 18 as a result of the balanced or symmetrical type structure of the conduit 18. As this occurs some of the exhaled gas will pass into the fixed volume chamber 36 and to a minor degree will be mixed with a minor amount of oxygen remaining in the conduit 18 at the close of the prior inhalation cycle as it passes into the fixed volume chamber 38.

Preferably the flow through the tube 14 into the channel 40 at this time will be such that this initial exhaled gas will not flow into the tube 14 but will flow into the variable chamber 38. This will cause the diaphragm 50 to move to increase the effective volume of this chamber 38 to the extent necessary for the diaphragm 50 to fit against the cover 54. As this occurs some minor amount of oxygen will, of course, tend to move through the tube 14 and the flow channel 40 so as to be mixed with the gas moving into the chamber 58.

After the variable volume chamber 38 and the conduit 18 become filled the gas expired during the continuation of the exhalation cycle will preferentially flow past the cannula 62 to the ambient. Substantially concurrently the flow into the holder 12 from the tube 14 will tend to cause oxygen to move into the ends 48 through the conduit 18 so as to displace exhaled gas which has become trapped within the conduit 18 out through the cannula 62 where this displaced gas will be entrained with other exhaled gas flowing to the ambient so as to be carried externally of the apparatus 10.

It is considered important to form the baffles 34 of a curved shape more or less as shown and to space them with respect to the openings 46 so that these baffles 34 will direct the incoming oxygen from the flow channel 40 directly into the ends 48 in such a manner as to minimize any chances of mixing of the oxygen with the exhaled gas trapped within the variable volume chamber 38 after this chamber has been filled. For maximum efficiency there should be substantialy no flow into the chamber 38 at this time. The fixed volume chamber 36 should, in general, be as small as reasonably possible so as to minimize the mixing of the two gases. It is used primarily to segregate flow from the flow channel 40 to the ends 48 from the remainder of the holder 12 to as great a degree as reasonably possible to minimize this mixing.

These factors are considered to be important in obtaining a high oxygen concentration in the conduit 18. The objective of this type of structure is to effectively utilize the momentum of the oxygen flowing through the flow channel 40 to displace exhaled gas in the conduit 18 in such a manner as to minimize mixing of the oxygen with exhaled gas. Because of the function of the baffles 34 in directing oxygen they serve more or less as nozzles conveying the incoming oxygen to the ends 48. These ends 48 should be spaced closely to the baffles 34 and the channel 40 to minimize mixing of oxygen as it is being directed toward those ends 48 so that there is substantially no flow of oxygen into the chamber 38 after this chamber 38 is filled. The momentum of the oxygen flow into the ends 48 should be reduced as little as possible in order to facilitate exhaled gas being displaced from the conduit 18 with minimal mixing.

Preferably the internal volume of the conduit 18 will be chosen with reference to the needs of a user of the apparatus 10 so as to be capable of holding a volume of gas corresponding to the minimum volume of oxygen which is most effective at the start of an inhalation cycle in maintaining a given desired oxygen saturation content of the blood. This volume will, of course, vary somewhat in accordance with the physical dimensions of an individual. It is presently considered that a volume of about 20 ml. within the interior of the conduit is most desirable in fulfilling the needs of a usual person needing oxygen therapy but that effective results under normal circumstances can be achieved having this conduit of a volume of from about 15 to about 50 ml.

This volume is important and should be related to the flow rate of the oxygen through the tube 14. This flow rate should be such that the oxygen will substantially dispace any exhaled gas during the last part of the breathing cycle after the variable chamber 38, the fixed chamber 36 and the conduit 18 have initially charged or filled with exhaled gas. The flow rate of the oxygen should preferably be sufficiently low so that substantially no oxygen during the course of exhalation flows out through the cannula 62 to be vented to the ambient with exhaled gas flowing to the ambient at this point.

Because of the placement of the cannula 62 at the start of inhalation the gas within the conduit 18 will be inhaled preferentially instead of the ambient gas. Thus, the first gas inhaled will consist of the oxygen accumulated within the conduit 18 and such vestiges of exhaled gas as may not have been displaced from it. This initial "charge" of gas will be followed by gas from within the variable chamber 38 as this chamber collapses and limited oxygen delivered through the tube 14 until such time as the variable chamber 38 has completely collapsed. At this point the oxygen being delivered to the holder 12 will continue to be preferentially inhaled through the conduit 18 as ambient air is drawn in around the cannula 62.

With this mode of operation the oxygen within the conduit 18 which is accumulated during the closing part of exhalation will be delivered to the respiratory track at the start of inhalation so that this oxygen rich gas will go to the extremities of the lungs where it is effective in maintaining the oxygen level of the blood. The predominently exhaled gas which has accumulated within the variable volume chamber 38 during exhalation will act so as to more or less "displace" or "push"

the almost pure oxygen which has accumulated within the conduit 18 prior to inhalation so that it can effectively flow into the portions of the lung indicated.

In order for this latter volume within the chamber 38 to be effective in this regard it must be sufficiently large so as to be capable of replacing all of the gas within the conduit 18 during the initial stages of inhalation. In theory this dictates that the variable volume chamber 38 must be as large as the volume of the conduit 18 when the chamber 38 is fully expanded. As a practical matter the expanded volume of the chamber 38 should be somewhat greater than this to make sure that all of the oxygen rich gas is displaced from the conduit 18.

The volume of the gas within the chamber 38 and the weight of the diaphragm 50 should not be sufficiently large or great so that it significantly difficult for an individual to move because of its inertia and of the inertia of the diaphragm 50. As a consequence of this, the expanded volume of the chamber 38 should be as small as is reasonably effective to permit displacement of all of the gas within the conduit 18 in response to a minimal pressure change resulting from an individual breathing. It is presently considered that it is preferable for this expanded volume of the chamber 38 to be about 40 ml. but that acceptable results can be achieved if the volume of this chamber is from about 30 to about 50 ml.

On occasion the manner in which an individual breathes will make it desirable so that an assist be given to the partial vacuum created on inhalation which is used to withdraw oxygen rich gas from the conduit 18 into the lungs. Such an assist can be achieved by forming the diaphragm 50 of a resilient elastomeric material as indicated in the preceding discussion in such a manner that this diaphragm 50 is stretched slightly when the chamber 38 is filled or is nearly filled. When the diaphragm is formed in this manner the tendency of the diaphragm 50 to revert to its initial configuration will cause a pressure on the gas within the chamber 38 at the start of inhalation which will tend to overcome any inertia of either the gas within this chamber 38 or within the conduit 18 so as to facilitate the initial movement of the gasses involved. When the diaphragm 50 if formed so as to assist in causing gas flow at the start of inhalation it should be formed so that it is easily stretched in response to pressures as are developed during exhalation and so that it is only slightly stretched when expanded into contact with the portion 56 of the cover 54.

At the end of inhalation the cycle described in the preceding will, of course, recommence. When the apparatus 10 is used in the desired manner virtually the entire conduit 18 will be filled with substantially pure oxygen at the start of inhalation and this oxygen will be effectively used as described in the preceding. This is important in achieving economic benefit. Because of the size and bilaterally symmetrical shape of the holder 12 and the manner in which it is supported this holder normally is comparatively inconspicuous as it is used by a person. It can even be worn under various articles of clothing so as to be hidden from view. These factors are important from an aesthetic standpoint and aid in user acceptance of the apparatus 10.

Because of the precise conduit 18 structure described there is very little chance of this conduit becoming pinched off during normal use. Because the conduit 18 and the tube 14 are sealed to the rims 26 there is very little danger of the ends 44 and 48 becoming detached as the apparatus 10 is used. Further, because of the construction of the holder 12 there is virtually no reasonable chance of this holder being rendered inoperative or causing discomfort as a result of pressure being applied to it as the apparatus 12 is used.

We claim:

1. An apparatus which is primarily intended for use in oxygen therapy, said apparatus having a housing defining a gas holder therein, said housing including means interior thereof for providing a variable volume chamber capable of changing in volume in response to pressure resulting from the inhalation and exhalation of a person who is using said apparatus, a conduit means for conveying gas, an extremity of said conduit means being in communication with the interior of said variable volume chamber, the other extremity of said conduit means being adapted so as to receive expired air from said person and so as to be capable of supplying gas to said person and also provide a simultaneous flow of ambient air to and from said person, and supply means for supplying oxygen to said conduit means so that it will be supplied to said person during inhalation, said other extremity of said conduit means adapted to be spaced from the person so that expired air can be vented to the ambient during part of the exhalation cycle and so that ambient air can be inhaled during part of the inhalation cycle in which the improvement comprises:

said housing further including means defining a fixed volume chamber located adjacent to said variable volume chamber and opening means leading between said two chambers, said first mentioned extremity of said conduit means and said supply means both leading into said fixed volume chamber, baffle means in association with said fixed volume chamber for directing oxygen from said supply means into said first mentioned extremity of said conduit means, said baffle means being shaped so that when said variable volume chamber is filled there is substantially no flow of oxygen into said chamber as oxygen flows from said supply means.

2. An apparatus as claimed in claim 1 wherein:
said conduit means comprises an elongated flexible conduit having ends, both of said ends leading into said fixed chamber and a cannula means located on said conduit intermediate said ends of said conduit, said ends of said conduit constituting said first mentioned extremity, said cannula means constituting said other extremity.

3. An apparatus as claimed in claim 2 wherein:
said cannula means are constructed so as to permit air flow to and from the ambient when said apparatus is being used.

4. An apparatus as claimed in claim 1 wherein:
said variable volume chamber includes an elastomeric diaphram mounted in said housing and defining said variable volume chamber therewith which is capable of being stretched in response to pressure developed during exhalation.

5. An apparatus as claimed in claim 1 wherein:
said holder is a flat generally disk-like shaped housing and has an imporforate back which is overlayed by a perforate cover, said variable volume chamber comprising a portion of said back, a rim attached thereto within said cover and a flexible diaphragm secured across said rim, the space enclosed by said portion of said back, said rim and said diaphragm being connected by an opening to a peripheral portion of said housing between said back and said cover serving as said variable volume chamber.

6. An apparatus as claimed in claim 5 wherein:
said rim is an internal rim and said housing also includes a peripheral rim spaced from said internal rim, the space between said rims being enclosed so as to constitute a flow channel,
said supply means is a flexible supply line leading into a portion of said flow channel remote from said fixed chamber.

7. An apparatus as claimed in claim 5 wherein:
said diaphragm is an elastomeric diaphragm which is capable of being stressed in response to pressure developed during exhalation.

8. An apparatus as claimed in claim 1 wherein:
the volume of said conduit means is from about 15 to about 50 ml. and the volume of said variable volume chamber is from about 30 to about 50 ml.

9. An apparatus as claimed in claim 8 wherein:
said conduit means comprises an elongated flexible conduit having ends, both of said ends leading into said fixed chamber and a cannula means located on said conduit intermediate said ends of said conduit, said ends of said conduit constituting said first mentioned extremity, said cannula means constituting said other extremity.

10. An apparatus as claimed in claim 9 wherein:
said cannula means are constructed so as to permit air flow to and from the ambient when said apparatus is being used.

11. An apparatus as claimed in claim 8 wherein:
said housing is a flat generally disk-like shape and has an imporforate back which is overlayed by a perforate cover, said variable volume chamber comprising a portion of said back, a rim attached thereto within said cover and a flexible diaphragm secured across said rim, the space enclosed by said portion of said back, said rim and said diaphragm being connected by an opening to a peripheral portion of said housing between said back and said cover serving as said variable volume chamber.

12. An apparatus as claimed in claim 11 wherein:
said rim is an internal rim and said housing also includes a peripheral rim spaced from said internal rim, the space between said rims being enclosed so as to constitute a flow channel,
said supply means is a flexible supply line leading into a portion of said flow channel remote from said fixed chamber.

13. An apparatus as claimed in claim 1 wherein:
said conduit means comprises an elongated flexible conduit having ends, both of said ends leading into said fixed chamber and a cannula means located on said conduit intermediate said ends of said conduit, said ends of said conduit constituting said first mentioned extremity, said cannula means constituting said other extremity,
said housing is a flat generally disk-like shape and has an imporforate back which is overlayed by a perforate cover, said variable volume chamber comprising a portion of said back, a rim attached thereto within said cover and a flexible diaphragm secured across said rim, the space enclosed by said portion of said back, said rim and said diaphragm being connected by an opening to a peripheral portion of said housing between said back and said cover serving as said variable volume chamber.

14. An apparatus as claimed in claim 13 wherein:
said cannula means are constructed so as to permit air flow to and from the ambient when said apparatus is being used,
said rim is an internal rim and said housing includes a peripheral rim spaced from said internal rim, the space between said rims being enclosed so as to constitute a flow channel,
said supply means is a flexible supply line leading into a portion of said flow channel remote from said fixed chamber.

15. An apparatus as claimed in claim 14 wherein:
the volume of said conduit means is from about 15 to about 50 ml. and the volume of said variable volume chamber is from about 30 to about 50 ml.

16. An apparatus as claimed in claim 15 wherein:
said flow channel has two ends, each of said ends being located immediately adjacent to one of said ends of said conduit in said fixed volume chamber, said baffle means are associated with and adjacent to each of said ends of said flow channel.

* * * * *

UNITED STATES PATENT AND TRADEMARK OFFICE
CERTIFICATE OF CORRECTION

PATENT NO. : 4,572,177                                    Page 1 of 2

DATED      : FEBRUARY 25, 1986

INVENTOR(S): BRIAN L. TIEP, ROBERT E. PHILLIPS, BEN A. OTSAP

It is certified that error appears in the above-identified patent and that said Letters Patent is hereby corrected as shown below:

Column 1, line 9, after the number '432,187' change the word "entitled" to —filed—.

Column 1, line 37 and 56, "is" should be —has—.

Column 2, line 12, "disloged" should be —dislodged—.

Column 3, line 20, "indicated" should be —indicate—.

Column 3, line 45, "conmventional" should be —conventional—.

Column 4, line 31, "cource" should be —course—.

Column 5, line 2, "position" should be —positions—.

Column 5, line 44, "58" should be —38—.

Column 5, line 64, "substantialy" should be —substantially—.

Column 6, line 38, "dispace" should be —displace—.

Column 6, line 54, "limited" should be —limits—.

Column 6, line 66, "predominently" should be —predominantly—.

Column 7, line 16, after "it" add the word —is—.

Column 7, line 42, "if" should be —is—.

Column 8, line 60, "imporforate" should be —imperforate—

UNITED STATES PATENT AND TRADEMARK OFFICE
CERTIFICATE OF CORRECTION

PATENT NO. : 4,572,177    Page 2 of 2

DATED : February 25, 1986

INVENTOR(S) : BRIAN L. TIEP, ROBERT E. PHILLIPS, BEN A. OTSAP

It is certified that error appears in the above-identified patent and that said Letters Patent is hereby corrected as shown below:

Column 9, line 33, "imporforate" should be --imperforate--.

Column 10, line 15, "imporforate" should be --imperforate--.

Signed and Sealed this

First Day of July 1986

[SEAL]

Attest:

Attesting Officer

DONALD J. QUIGG

Commissioner of Patents and Trademarks